(12) United States Patent
Nelson et al.

(10) Patent No.: US 6,171,333 B1
(45) Date of Patent: Jan. 9, 2001

(54) HEATING AND COOLING COMFORTER

(76) Inventors: Merle D. Nelson; Linda F. Nelson, both of 1616 Cedar La., Augusta, KS (US) 67010

( * ) Notice: Under 35 U.S.C. 154(b), the term of this patent shall be extended for 0 days.

(21) Appl. No.: 09/301,730

(22) Filed: Apr. 29, 1999

(51) Int. Cl.[7] ............................. A61F 7/00; A47G 20/02
(52) U.S. Cl. ......................... 607/104; 607/107; 5/502; 5/652.2; 5/655.3; 5/485; 5/652.1
(58) Field of Search ................. 5/652.1, 652.2, 5/655.3, 502, 485, 488; 607/104, 114, 107, 96

(56) References Cited

U.S. PATENT DOCUMENTS

| | | | |
|---|---|---|---|
| 2,512,559 | * | 6/1950 | Williams ................................. 5/347 |
| 2,601,189 | * | 6/1952 | Wales ...................................... 4/160 |
| 3,486,177 | * | 12/1969 | Marshack ............................... 5/347 |
| 4,660,388 | * | 4/1987 | Greene, Jr. ............................ 62/261 |
| 4,867,230 | * | 9/1989 | Voss ....................................... 165/46 |
| 5,265,599 | * | 11/1993 | Stephenson et al. ................. 607/104 |
| 5,392,847 | * | 2/1995 | Stephenson ............................ 607/14 |
| 5,443,488 | * | 8/1995 | Namenye et al. .................... 607/104 |
| 5,473,783 | * | 12/1995 | Allen ....................................... 5/469 |
| 5,655,237 | * | 8/1997 | Suzuki et al. .......................... 5/502 |
| 5,675,848 | * | 10/1997 | Kappel .................................... 5/482 |
| 5,728,145 | * | 3/1998 | Phlipot et al. ....................... 607/104 |
| 5,800,489 | * | 9/1998 | Augustine ............................ 607/107 |

* cited by examiner

*Primary Examiner*—Linda C. M. Dvorak
*Assistant Examiner*—Jocelyn Debra Ram

(57) ABSTRACT

A heating and cooling comforter for heating or cooling a user. The heating and cooling comforter includes an inner bladder comprising a pair of panels coupled together along the outer perimeter of the inner bladder to define an air space therebetween. Each of the panels of the inner bladder has a plurality of spaced apart air apertures therethrough into the air space of the inner bladder. A comforter cover is also included comprising a pair of panels coupled together along the outer perimeter of the comforter cover. The comforter cover has an elongate slit therein between the panels of the comforter cover. The inner bladder is inserted into the comforter cover. A vent cover is included having an arcuate upper wall and an open bottom. An elongate conduit is extended between the from the inner bladder and the vent cover to fluidly connect the air space of the inner bladder to the vent cover.

8 Claims, 3 Drawing Sheets

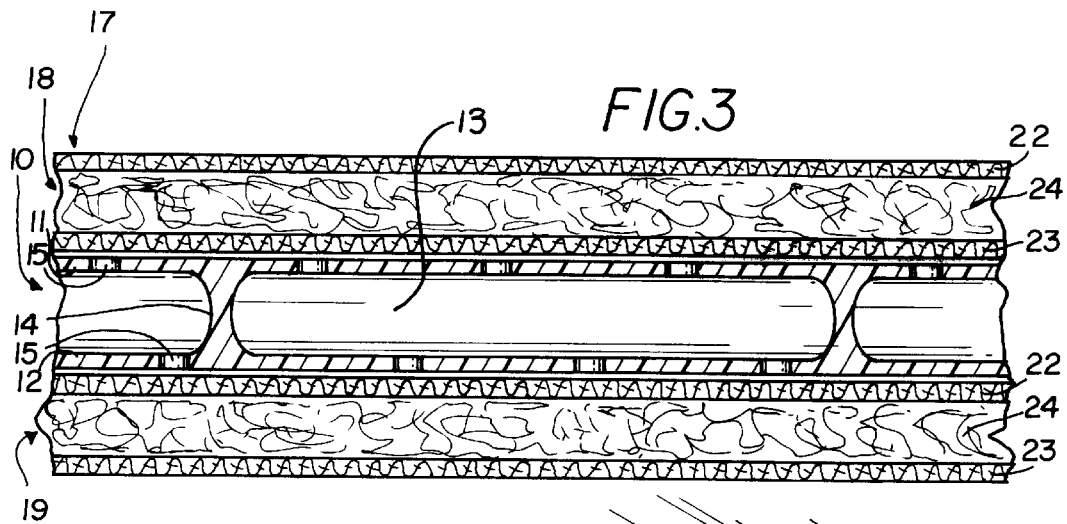
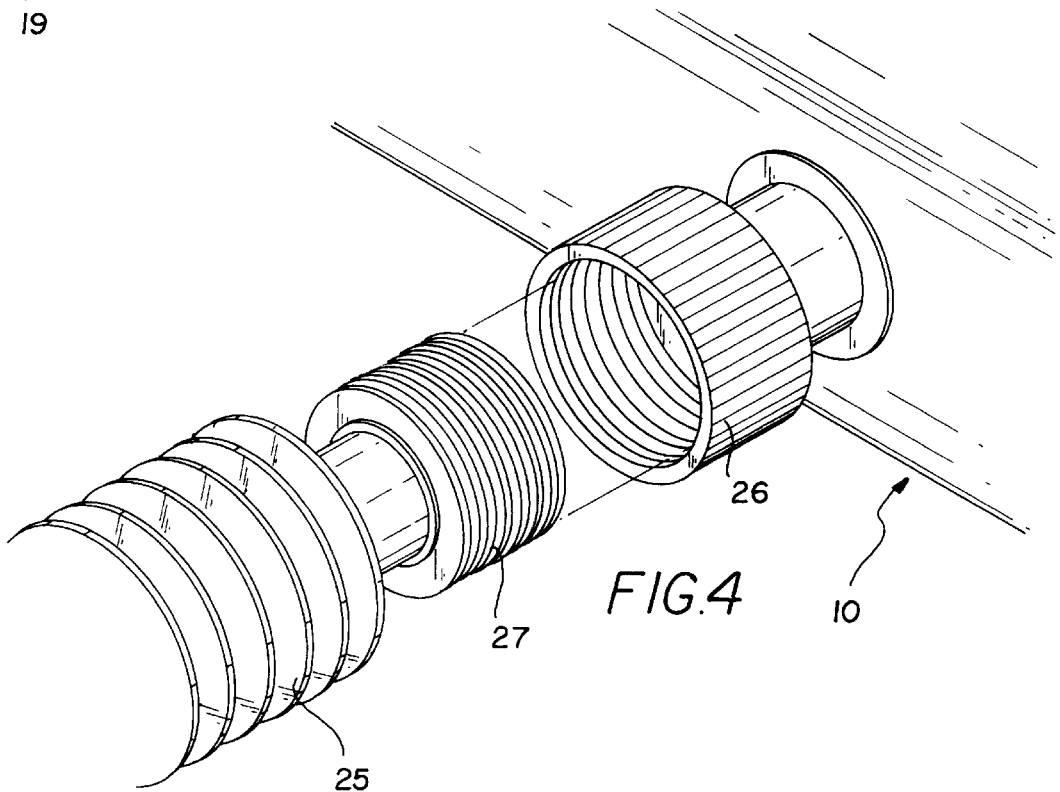

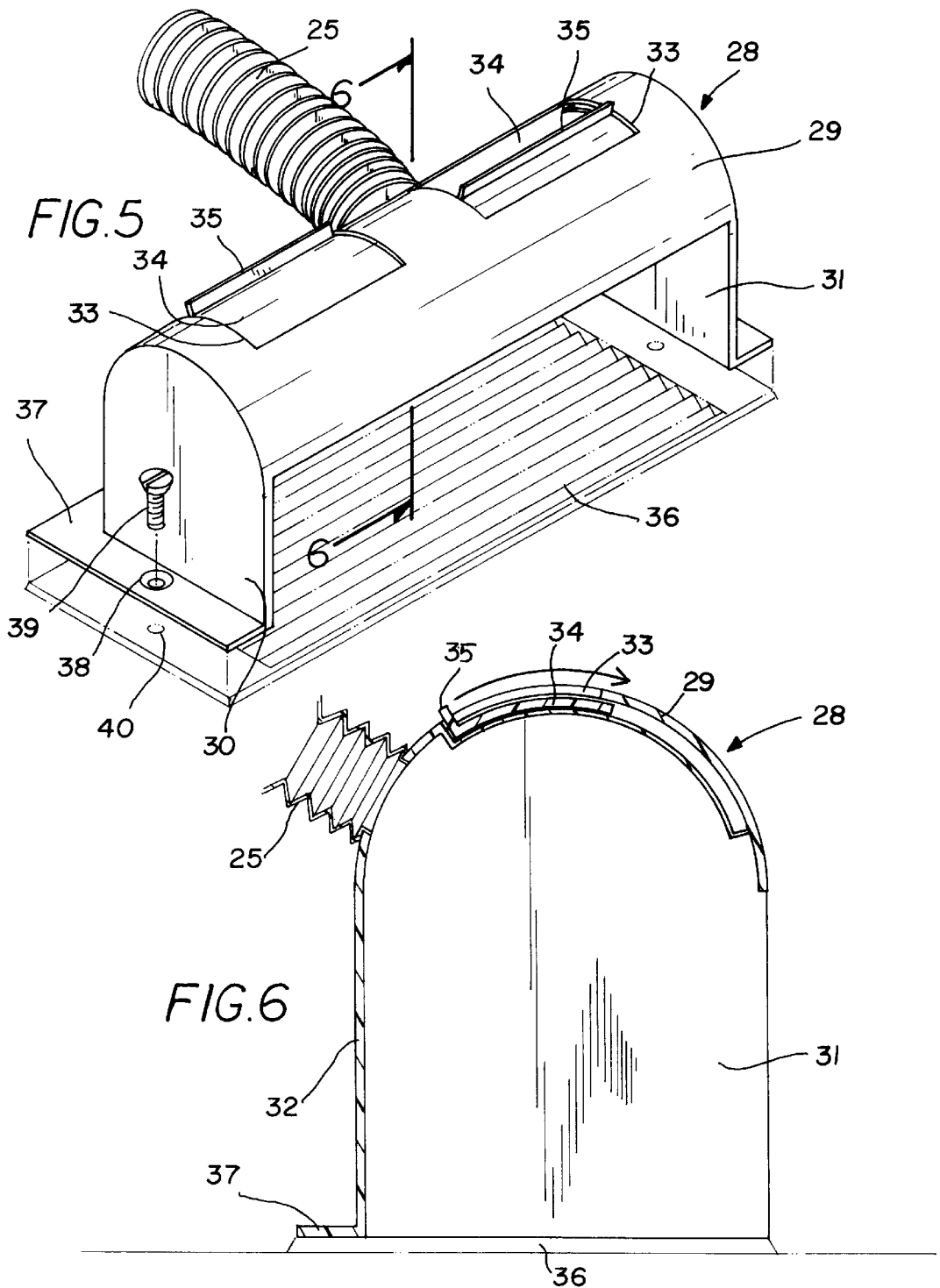

HEATING AND COOLING COMFORTER

BACKGROUND OF THE INVENTION

1. Field of the Invention

The present invention relates to comforters and more particularly pertains to a new heating and cooling comforter for heating or cooling a user.

2. Description of the Prior Art

The use of comforters is known in the prior art. More specifically, comforters heretofore devised and utilized are known to consist basically of familiar, expected and obvious structural configurations, notwithstanding the myriad of designs encompassed by the crowded prior art which have been developed for the fulfillment of countless objectives and requirements.

Known prior art includes U.S. Pat. Nos. 5,728,145; 4,997,230; 5,794,683; 5,350,417; 5,697,963; and U.S. Pat. No. Des. 359,810.

While these devices fulfill their respective, particular objectives and requirements, the aforementioned patents do not disclose a new heating and cooling comforter. The inventive device includes an inner bladder comprising a pair of panels coupled together along the outer perimeter of the inner bladder to define an air space therebetween. Each of the panels of the inner bladder has a plurality of spaced apart air apertures therethrough into the air space of the inner bladder. A comforter cover is also included comprising a pair of panels coupled together along the outer perimeter of the comforter cover. The comforter cover has an elongate slit therein between the panels of the comforter cover. The inner bladder is inserted into the comforter cover. A vent cover is included having an arcuate upper wall and an open bottom. An elongate conduit is extended between the inner bladder and the vent cover to fluidly connect the air space of the inner bladder to the vent cover.

In these respects, the heating and cooling comforter according to the present invention substantially departs from the conventional concepts and designs of the prior art, and in so doing provides an apparatus primarily developed for the purpose of heating or cooling a user.

SUMMARY OF THE INVENTION

In view of the foregoing disadvantages inherent in the known types of comforters now present in the prior art, the present invention provides a new heating and cooling comforter construction wherein the same can be utilized for heating or cooling a user.

The general purpose of the present invention, which will be described subsequently in greater detail, is to provide a new heating and cooling comforter apparatus and method which has many of the advantages of the comforters mentioned heretofore and many novel features that result in a new heating and cooling comforter which is not anticipated, rendered obvious, suggested, or even implied by any of the prior art comforters, either alone or in any combination thereof.

To attain this, the present invention generally comprises an inner bladder comprising a pair of panels coupled together along the outer perimeter of the inner bladder to define an air space therebetween. Each of the panels of the inner bladder has a plurality of spaced apart air apertures therethrough into the air space of the inner bladder. A comforter cover is also included comprising a pair of panels coupled together along the outer perimeter of the comforter cover. The comforter cover has an elongate slit therein between the panels of the comforter cover. The inner bladder is inserted into the comforter cover. A vent cover is included having an arcuate upper wall and an open bottom. An elongate conduit is extended between the inner bladder and the vent cover to fluidly connect the air space of the inner bladder to the vent cover.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new heating and cooling comforter apparatus and method which has many of the advantages of the comforters mentioned heretofore and many novel features that result in a new heating and cooling comforter which is not anticipated, rendered obvious, suggested, or even implied by any of the prior art comforters, either alone or in any combination thereof.

It is another object of the present invention to provide a new heating and cooling comforter which may be easily and efficiently manufactured and marketed.

It is a further object of the present invention to provide a new heating and cooling comforter which is of a durable and reliable construction.

An even further object of the present invention is to provide a new heating and cooling comforter which is susceptible of a low cost of manufacture with regard to both materials and labor, and which accordingly is then susceptible of low prices of sale to the consuming public, thereby making such heating and cooling comforter economically available to the buying public.

Still yet another object of the present invention is to provide a new heating and cooling comforter which provides in the apparatuses and methods of the prior art some of the advantages thereof, while simultaneously overcoming some of the disadvantages normally associated therewith.

Still another object of the present invention is to provide a new heating and cooling comforter for heating or cooling a user.

Yet another object of the present invention is to provide a new heating and cooling comforter which includes an inner bladder comprising a pair of panels coupled together along the outer perimeter of the inner bladder to define an air space therebetween. Each of the panels of the inner bladder has a plurality of spaced apart air apertures therethrough into the air space of the inner bladder. A comforter cover is also included comprising a pair of panels coupled together along the outer perimeter of the comforter cover. The comforter cover has an elongate slit therein between the panels of the comforter cover. The inner bladder is inserted into the comforter cover. A vent cover is included having an arcuate upper wall and an open bottom. An elongate conduit is extended between the inner bladder and the vent cover to fluidly connect the air space of the inner bladder to the vent cover.

Still yet another object of the present invention is to provide a new heating and cooling comforter that is used in conjunction with a forced air central air system to use heated or cooled air of the forced air central air system to heat and cool the comforter.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 3 is a schematic cross sectional view of the present invention.

FIG. 4 is a schematic enlarged exploded perspective view of the connection between the conduit and the inner bladder.

FIG. 5 is a schematic perspective view of the vent cover of the present invention.

FIG. 6 is a schematic cross sectional view of the vent cover taken from line 6—6 of FIG. 5.

DESCRIPTION OF THE PREFERRED EMBODIMENT

With reference now to the drawings, and in particular to FIGS. 1 through 6 thereof, a new heating and cooling comforter embodying the principles and concepts of the present invention will be described.

As best illustrated in FIGS. 1 through 6, the heating and cooling comforter generally comprises an inner bladder comprising a pair of panels coupled together along the outer perimeter of the inner bladder to define an air space therebetween. Each of the panels of the inner bladder has a plurality of spaced apart air apertures therethrough into the air space of the inner bladder. A comforter cover is also included comprising a pair of panels coupled together along the outer perimeter of the comforter cover. The comforter cover has an elongate slit therein between the panels of the comforter cover. The inner bladder is inserted into the comforter cover. A vent cover is included having an arcuate upper wall and an open bottom. An elongate conduit is extended between the from the inner bladder and the vent cover to fluidly connect the air space of the inner bladder to the vent cover.

In closer detail, a generally rectangular inner bladder 10 is provided having a generally rectangular outer perimeter comprising a pair of shorter ends, and a pair of longer sides extending between the ends of the inner bladder. The inner bladder comprises a pair of generally rectangular flexible panels 11,12 coupled together along the outer perimeter of the inner bladder to define an air space 13 therebetween. Ideally, the inner bladder comprises a flexible plastic material.

Preferably, as illustrated in FIG. 3, the inner bladder has a plurality of stalactiform resilient deformable spacers 14 in the air space of the inner bladder and extending between the panels of the inner bladder to space the panels of the inner bladder apart from one another.

Figure 1:
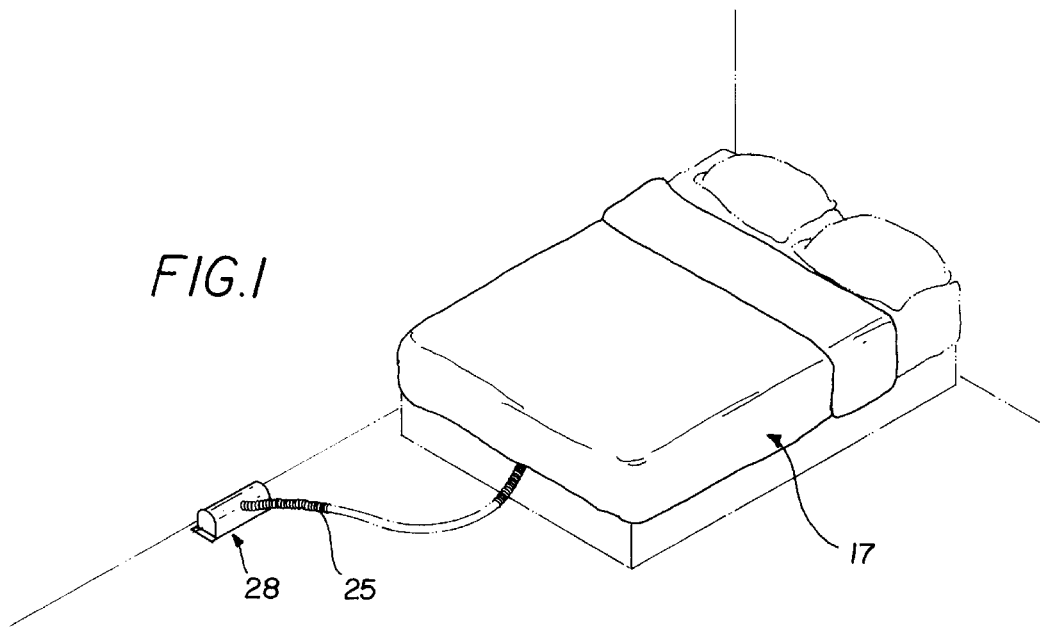
FIG. 1 is a schematic perspective view of a new heating and cooling comforter in use connected to a vent register of a central air system and on a bed of a user according to the present invention.
Figure 2:
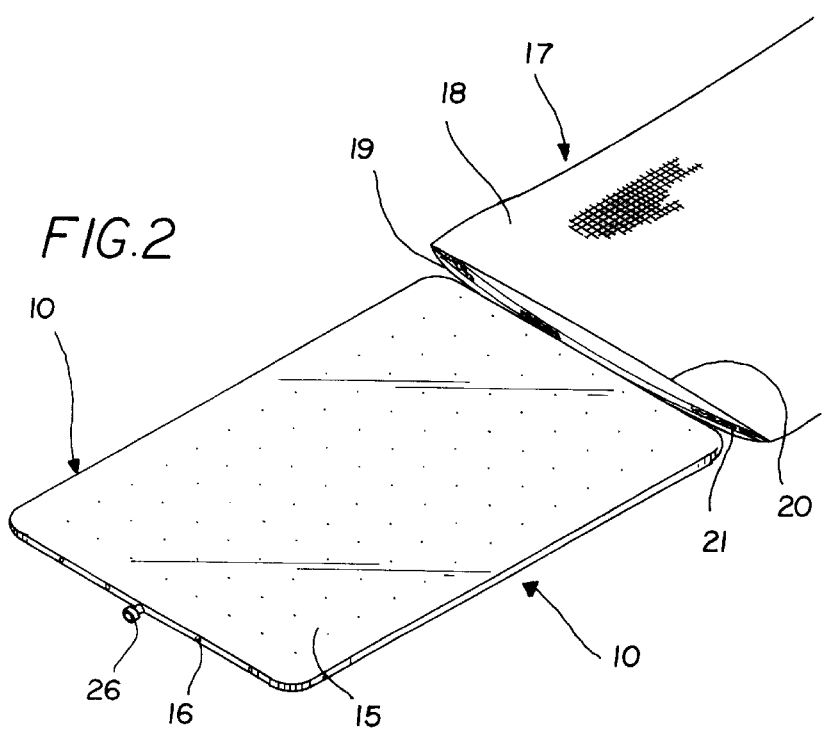
FIG. 2 is a schematic exploded perspective view of the present invention.

Each of the panels of the inner bladder has a plurality of spaced apart air apertures 15 therethrough into the air space of the inner bladder to permit passage of air out of the air space of the inner bladder through the air apertures. As best illustrated in FIG. 2, the air apertures of each panel of the inner bladder are ideally arranged in a generally rectangular grid-like fashion on the respective panel of the inner bladder comprises a plurality of rows of spaced apart air apertures and a plurality of columns of spaced apart air apertures extending substantially perpendicular to the rows of spaced apart air apertures of the respective panel of the inner bladder. In this ideal embodiment, the air apertures are preferably spaced apart at generally equal intervals in the respective row and column of air apertures.

Preferably, at least one end of the inner bladder has a plurality of spaced apart drain holes 16 into the air space of the inner bladder.

A generally rectangular comforter cover 17 is provided having a generally rectangular outer perimeter comprising a pair of shorter ends, and a pair of longer sides extending between the ends of the comforter cover. The comforter cover comprises a pair of generally rectangular flexible fabric material panels 18,19 coupled together along the outer perimeter of the comforter cover. The comforter cover has an elongate slit 20 therein between the panels of the comforter cover along one of the ends of the comforter cover. The comforter cover preferably has a fastener 21 (such as a zipper, a hook and loop fastener or even buttons) for closing the elongate slit of the comforter cover.

Preferably, as illustrated in FIG. 3, each of the panels of the comforter cover comprises a pair of quilted fabric material outer layers 22,23 and a down or cotton fill inner layer 24 interposed between the outer layers of the respective panel of the comforter cover.

The inner bladder is inserted into the comforter cover such that the comforter cover substantially covers the inner bladder. One of the ends of the inner bladder is positioned adjacent the slit of the comforter cover and has a flexible corrugated tubular elongate conduit 25 extending therefrom.

The elongate conduit has a pair of opposite ends. With reference to FIG. 4, one of the ends of elongate conduit is detachably coupled to the one end of the inner bladder ideally by a threaded female connector 26 on the inner bladder and a male threaded connector 27 on the end of the elongate conduit to fluidly connect the elongate conduit to the air space of the inner bladder.

The system also includes a vent cover 28 having an arcuate upper wall 29, a pair of generally D-shaped end walls 30,31, a generally rectangular side wall 32 extending between the end walls of the vent cover, an generally rectangular open bottom, and a generally rectangular open side in communication with the open bottom of the vent cover. As best illustrated in FIGS. 5 and 6, the other end of the elongate conduit is coupled to the upper wall of the vent cover adjacent the side wall of the vent cover to fluidly connect the elongate conduit to the vent cover.

Preferably, the upper wall of the vent cover has a pair of generally rectangular vent openings 33 and a pair of slidably mounted door panels 34 closing the vent openings. Even more preferably, each of the door panels has a finger tab 35 upwardly extending therefrom.

In use, the system is designed for use with a generally rectangular vent register 36 fluidly connected to a forced air central air system. As best illustrated in FIG. 5, the open bottom of the vent cover is positioned over the vent register such that the vent cover covers the vent register and so that air (either heated or cooled) from the central air system blown out of the vent register is blown into the vent cover and into the elongate conduit. In use, air blown into the elongate conduit via the vent cover is blown into the air space of the inner bladder and then subsequently is blown out of the air apertures of the panels of the inner bladder to heat the comforter cover and thus the user when heated air is used and to cool the comforter cover and thus the user when cooled air is used.

Preferably the vent cover has an outwardly extending lower flange 37 along the end walls and the side wall of the vent cover. The lower flange is coupled to the vent register. In a preferred embodiment, the lower flange of the vent cover has at least one mounting hole 38 through which a threaded fastener 39 is extended through the mounting hole and into a corresponding hole 40 in the vent register to couple the lower flange to the vent register.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

We claim:

1. A comforter heating and cooling system, comprising:
an inner bladder having an outer perimeter and comprising a pair of panels coupled together along said outer perimeter of said inner bladder to define an air space therebetween;
each of said panels of said inner bladder having a plurality of spaced apart air apertures therethrough into said air space of said inner bladder;
a comforter cover having an outer perimeter and comprising a pair of panels coupled together along said outer perimeter of said comforter cover;
said comforter cover having an elongate slit therein between said panels of said comforter cover;
said inner bladder being inserted into said comforter cover;
a vent cover having an arcuate upper wall and an open bottom; and
an elongate conduit being extended between said inner bladder and said vent cover to fluidly connect said air space of said inner bladder to said vent cover.

2. The comforter heating and cooling system of claim 1, wherein said inner bladder has a plurality of resilient deformable spacers in said air space of said inner bladder and extending between said panels of said inner bladder.

3. The comforter heating and cooling system of claim 1, wherein said air apertures of each panel of said inner bladder being arranged in a generally rectangular grid-like fashion on the respective panel of said inner bladder comprising a plurality of rows of spaced apart air apertures and a plurality of columns of spaced apart air apertures extending substantially perpendicular to said rows of spaced apart air apertures of the respective panel of said inner bladder.

4. The comforter heating and cooling system of claim 3, wherein said air apertures are spaced apart at generally equal intervals in the respective row and column of air apertures.

5. The comforter heating and cooling system of claim 1, wherein said comforter cover has a fastener for closing said elongate slit of said comforter cover.

6. The comforter heating and cooling system of claim 1, wherein each of said panels of said comforter cover comprises a pair of quilted fabric material outer layers and a down fill inner layer interposed between said outer layers of the respective panel of said comforter cover.

7. The comforter heating and cooling system of claim 1, wherein said upper wall of said vent cover has a pair of vent openings and a pair of slidably mounted door panels closing said vent openings.

8. A comforter heating and cooling system, comprising:
a generally rectangular inner bladder having a generally rectangular outer perimeter comprising a pair of ends, and a pair of sides extending between said ends of said inner bladder, said inner bladder comprising a pair of generally rectangular flexible panels coupled together along said outer perimeter of said inner bladder to define an air space therebetween;
said inner bladder having a plurality of resilient deformable spacers in said air space of said inner bladder and extending between said panels of said inner bladder;
each of said panels of said inner bladder having a plurality of spaced apart air apertures therethrough into said air space of said inner bladder;
said air apertures of each panel of said inner bladder being arranged in a generally rectangular grid-like fashion on the respective panel of said inner bladder comprising a plurality of rows of spaced apart air apertures and a plurality of columns of spaced apart air apertures extending substantially perpendicular to said rows of spaced apart air apertures of the respective panel of said inner bladder;

said air apertures being spaced apart at generally equal intervals in the respective row and column of air apertures;

a generally rectangular comforter cover having a generally rectangular outer perimeter comprising a pair of ends, and a pair of sides extending between said ends of said comforter cover, said comforter cover comprising a pair of generally rectangular flexible fabric material panels coupled together along said outer perimeter of said comforter cover;

said comforter cover having an elongate slit therein between said panels of said comforter cover along one of said ends of said comforter cover;

said comforter cover having a fastener for closing said elongate slit of said comforter cover;

each of said panels of said comforter cover comprising a pair of quilted fabric material outer layers and a down fill inner layer interposed between said outer layers of the respective panel of said comforter cover;

said inner bladder being inserted into said comforter cover such that said comforter cover substantially covers said inner bladder;

one of said ends of said inner bladder being positioned adjacent said slit of said comforter cover and having a flexible corrugated tubular elongate conduit extending therefrom;

said elongate conduit having a pair of opposite ends, one of said ends of elongate conduit being detachably coupled to said one end of said inner bladder to fluidly connect said elongate conduit to said air space of said inner bladder;

a vent cover having an arcuate upper wall, a pair of end walls, a side wall extending between said end walls of said vent cover, an generally rectangular open bottom, and a generally rectangular open side in communication with said open bottom of said vent cover;

the other end of said elongate conduit being coupled to said upper wall of said vent cover adjacent said side wall of said vent cover to fluidly connect said elongate conduit to said vent cover;

said upper wall of said vent cover having a pair of vent openings and a pair of slidably mounted door panels closing said vent openings;

a vent register fluidly connected to a central air system, said open bottom of said vent cover being positioned over said vent register such that said vent cover covers said vent register and so that air from said central air system blown out of said vent register is blown into said vent cover and into said elongate conduit, wherein air blown into said elongate conduit via said vent cover being blown into said air space of said inner bladder and then subsequently being blown out of said air apertures of said panels of said inner bladder; and said vent cover having an outwardly extending lower flange along said end walls and said side wall of said vent cover, said lower flange being coupled to said vent register.

* * * * *